United States Patent [19]

Fabbri

[11] Patent Number: 4,706,014

[45] Date of Patent: Nov. 10, 1987

[54] CAPACITIVE DEVICES FOR MEASURING THE DIAMETER OF A DIELECTRIC FIBER

[75] Inventor: Bruno Fabbri, Turin, Italy

[73] Assignee: CSELT - Centro Studi e Laboratori Telecomunicazioni S.p.A., Turin, Italy

[21] Appl. No.: 762,157

[22] Filed: Aug. 2, 1985

[30] Foreign Application Priority Data

Sep. 6, 1984 [IT] Italy .................. 67878 A/84

[51] Int. Cl.$^4$ .................. G01B 7/08; G01R 27/26
[52] U.S. Cl. .................. 324/61 P; 73/160
[58] Field of Search .................. 73/160, 159; 340/870.37; 361/280, 292, 300; 324/61 P, 61 R, 202, 230, 452, 217, 218

[56] References Cited

U.S. PATENT DOCUMENTS 2,992,392 7/1961 Haynes .................. 324/61 P
3,221,171 11/1965 Locher .................. 324/61 P
3,922,601 11/1975 Martin .................. 324/61 P

FOREIGN PATENT DOCUMENTS 0690283 10/1979 U.S.S.R. .................. 324/61 P

Primary Examiner—Reinhard J. Eisenzopf
Assistant Examiner—Jose M. Solis
Attorney, Agent, or Firm—Karl F. Ross; Herbert Dubno

[57] ABSTRACT

The improvements relating to capacitive devices for measuring the diameter of a dielectric fiber are based on a particular shaping of the capacitor plates, such as to allow electric field reductions at the edges to be compensated for and hence capacitance measurements to be unaffected by fibre vibrations.

5 Claims, 4 Drawing Figures

CAPACITIVE DEVICES FOR MEASURING THE DIAMETER OF A DIELECTRIC FIBER

FIELD OF THE INVENTION

The present invention relates to electrical devices for the remote measurement of the physical dimensions of an object and in particular it relates to an improvement in capacitive devices for measuring the diameter of a dielectric fiber.

BACKGROUND OF THE INVENTION

It is known that during dielectric-fiber drawing, plant equipment must be adjusted so as to obtain a uniform section fiber, and in case of circular section, a constant diameter fiber. Manually or automatically effected corrections of possible variations in physical fiber dimensions require a continuous and up-dated knowledge of the values of the dimensions. Yet, the measurements must not interfere with the fabrication process. Hence, contact measurements are to be avoided. In this case, as is known, remote measurements can be made, using optical or electric methods.

An electric measuring apparatus is described in Italian Patent Application No. 67936-A/81, filed on July 6, 1981, in the name of the Applicant and published on Feb. 12, 1983 as European Patent Application, with the publication No. 69332. In this apparatus a fiber, while being drawn, is caused to pass between the plates of a parallel-plate capacitor, and detection is effected of capacitance variations due to the changes in the effective dielectric constant of the space between the plates, caused by the introduction of the fiber into said space and by diameter variations along the fiber which, together with air or another gas contained in the space between the two plates, forms the capacitor dielectric.

The magnitude of the diameter or of diameter variations is derived from the capacitance variations. A number of disadvantages are encountered when using such apparatus in a manufacturing plant, owing to vibration of the fibres while passing between the capacitor plates. Such vibrations cause variations in the capacitance of the measuring capacitor and hence may be erroneously read as diameter variations.

This phenomenon is due to a lower electric field intensity near the plate edges, where the lines of force bend and are more widely separated. Thus, electric capacitance depends also on the position of the dielectric fibre between the plates and decreases when the dielectric-fiber axis, in its translatory movement orthogonal to the electric field, moves closer to the edges. Thus the fiber may appear to be smaller than it actually is.

This disadvantage cannot be overcome by increasing the distance between the plate edges and the fiber under test, as this entails plate expansion and hence an increase in the capacitance C of the capacitor. This capacitance increase is detrimental to sensitivity and, hence, to a precise measurement. In fact the relative capacitance variation $(\Delta C)/C$, due to the introduction of the optical fiber with radius a into the space between the plates is given by the formula $$(\Delta C)/C = (\pi a^2)/S \cdot (\epsilon_1 - \epsilon_0)/(\epsilon_1 + \epsilon_0) \qquad (1)$$

where S is the surface of the section, orthogonal to the capacitor plates, assumed to be rectangular, and to the fibre axis, $\epsilon_1$ is the dielectric constant of the material of the fibre, $\epsilon_0$ is the dielectric constant of the medium (air or another gas) which surrounds the fibre in the space between the two capacitor plates, and C is the capacitance of the capacitor when the dielectric is wholly a medium of dielectric constant $\epsilon_0$.

From formula (1) it will be apparent that such relative variation is inversely proportional to S, which therefore is to be kept small. For example, in an apparatus using a capacitor with a capacity of 1 pF, there is a variation of about 0.003 pF after the introduction of a fibre having a diameter of about 125 $\mu$m and dielectric constant $\epsilon_1$ equal to about 4, while the measuring instrument must possess enough sensitivity to detect diameter variations of 1/1000 and hence capacity variation of $6 \cdot 10^{-6}$ pF.

It is to be noted that the vibration component which is in the plane parallel to the plates is usually more detrimental than that in the perpendicular plane; however, it is advisable to minimize the effects due to both components.

In addition to capacitance variations due to fiber vibrations, there are also variations due to thermal expansion of plates and of other structures forming the capacitor and variations due to measuring instruments, for which suitable compensation should be provided.

SUMMARY OF THE INVENTION

These and other disadvantages are overcome by the improvements to capacitive devices for measuring the diameter of a dielectric fibre provided by the present invention which allows the effects of dielectric-fiber vibrations to be minimized. The capacitive means can be easily built and are easily installed and adjusted in the measuring device, so as to allow a significant detection of diameter variations in the order of $10^{-7}$ m, when the fibers move within most of the space comprised between the plates.

The present invention provides improvements relating to capacitive devices for measuring the diameter of a dielectric fiber, in which the capacitance variations due to changes in the dielectric properties of the space between the plates of a capacitor, caused by the introduction of the fiber into said space and by diameter variations along the fiber are measured. The capacitor comprises plates with extensions such as to generate regions with a strong electric field close to the edges, to compensate for variations of the field and hence minimize the effects of the dielectric-fiber vibrations in most of the space comprised between the plates.

BRIEF DESCRIPTION OF THE DRAWING

Further features of the invention will become apparent from the following description with reference to the annexed drawing in which.

SPECIFIC DESCRIPTION

Figure 1:
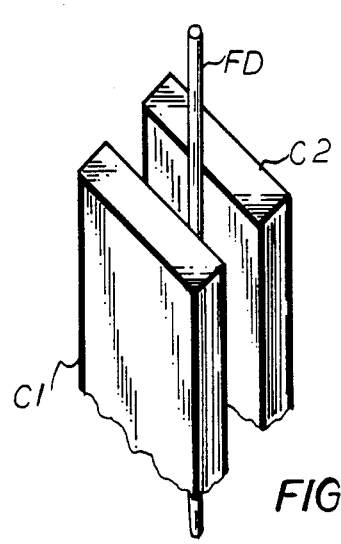
FIG. 1 is a perspective view of a conventional parallel-plate capacitor.

The method of compensating for the distortion of the electric field close to the plate edges consists in modifying the plate shape. More particularly, the distance from each other is decreased where the electric field of the equivalent parallel-plate capacitor of the type represented in FIG. 1 would be weaker. Plates are denoted by C1 and C2 and the dielectric fiber by FD.

Figure 2:
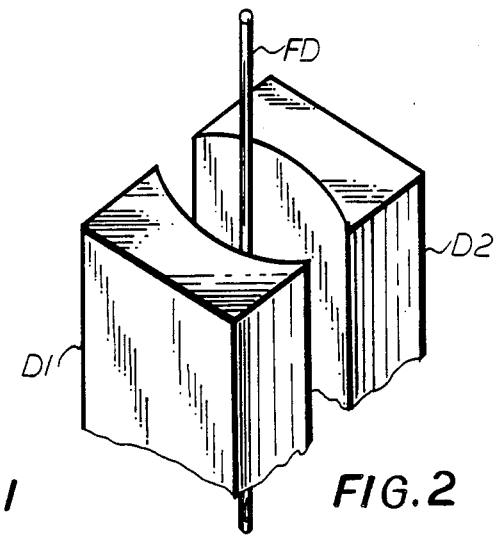
FIG. 2 is a perspective view of a first capacitor according to the invention.

A first embodiment of a capacitor modified according to the invention is represented in FIG. 2. Plates D1 and D2 have concave surfaces, with corresponding concavities facing each other. Extensions obtained at the edges cause the resulting electrical field to be uniform in a great portion of the space comprised between the plates.

Figure 3:
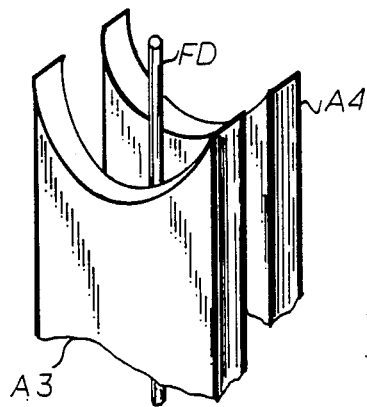
FIG. 3 is a perspective view of a second capacitor.

A second example of parallel-plate capacitor implemented according to the invention is shown in FIG. 3.

A3 and A4 are thin plates equipped with extensions at the ends, such as to generate regions with strong electrical field to compensate for decreases at the edges. Thanks to them the effect is obobtained of increasing fiber exposition length in peripheral capacitor regions. It is evident that during the initial adjustment phase a plate is kept fixed and the other is displaced till minimum sensitivity to vibrations of dielectric fibre FD is achieved.

These plates can be advantageously made of metallized quartz, thus achieving high stability with varying temperature.

A third embodiment of the invention (FIG. 4) makes use of a parallel-plate capacitor and electrical field distortions are compensated for by generating peaks of the electrical field in peripheral regions. In this way the fiber exposition length is increased in peripheral regions.

Figure 4:
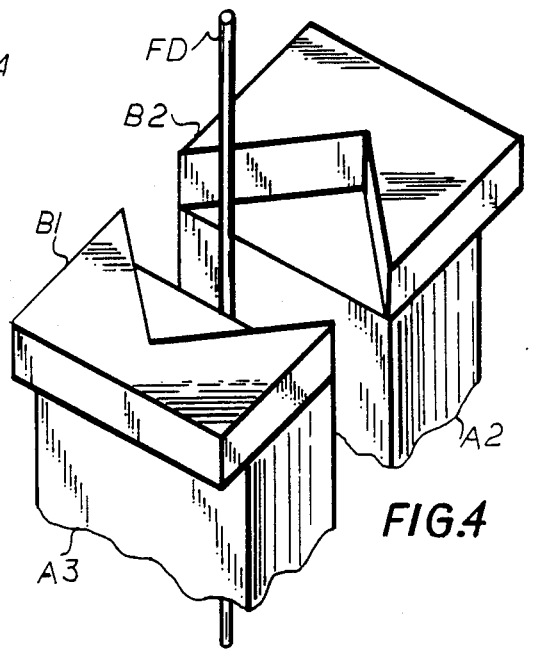
FIG. 4 is a perspective view of a third capacitor.

In FIG. 4, A1 and A2 denote the capacitor plates and B1, B2 two rectangular plates, whose length is nearly equal to capacitor-plate width and which are equipped with two extensions in correspondence with the extremities of a side. These plates are electrically connected to the capacitor plates in correspondence with the upper part and possibly an analogous pair can be placed in the inferior part of the capacitor, not shown.

The plates are placed such that the extensions face each other; there through the dielectric fiber FD is passed. These plates can be held in place by magnetic force, in a first adjusting step, by fabricating the various parts with suitable ferro-magnetic materials. They are eventually soldered together with suitable adhesives.

The modified capacitor is no longer sensitive to fibre FD vibrations, because electric field diminution at the edges is compensated for, in most of the space comprised between the plates, by strong electric-field regions existing between the extensions. As in the preceding case, these are such as to increase the fiber exposition length in peripheral capacitor regions, where the field is less strong. During the initial adjusting phase the fiber is caused to vibrate and the plates are moved till measuring instrument reads the minimum capacitance variation. Afterwards they are blocked in their final position.

What is claimed is:

1. In a device for the capacitive measurement of the diameter of a dielectric fiber in which capacitance variations due to changes in dielectric properties of a space between plates of a capacitor caused by the introduction of said fiber into said space are measured, the improvement wherein said capacitor comprises:

a pair of mutually parallel capacitor plates of rectangular cross section having spacedly juxtaposed confronting longitudinal wide sides straddling said fiber, rear wide sides parallel to said confronting wide sides, lateral narrow sides perpendicular to said wide sides of each capacitor plate, and respective rectangular end faces lying in a common plane at one end of each of said capacitor plates; and a pair of generally rectangular plates spacedly juxtaposed with one another and each seated on one of said end faces, said generally rectangular plates each having a length substantially equal to the width of the respective capacitor plate measured across the wide sides thereof and being electrically connected with the respective capacitor plate at the respective end face thereof, each of said generally rectangular plates having extensions along the respective narrow sides of the respective capacitor plate converging toward a plane of the respective confronting wide side to generate strong electrical fields between the converging extensions of the rectangular plates on the opposing capacitor plates to compensate for variations in an electrical field between said capacitor plates caused by vibration of said fiber.

2. The improvement defined in claim 1 wherein the converging extensions on each of said rectangular plates define a V-shaped notch in the respective rectangular plate opening toward the other rectangular plate.

3. The improvement defined in claim 2 wherein said rectangular plates are held on the respective capacitor plates by magnetic force.

4. The improvement defined in claim 2 wherein each of the rectangular plates is soldered to the respective capacitor plate.

5. The improvement defined in claim 2 wherein each of said capacitor plates is composed of metallized quartz.

* * * * *